(12) United States Patent
Gletsos

(10) Patent No.: US 6,384,223 B1
(45) Date of Patent: May 7, 2002

(54) SUBSTITUTED QUINAZOLINE DERIVATIVES

(75) Inventor: Constantine Gletsos, Pomona, NY (US)

(73) Assignee: American Home Products Corporation, Madison, NJ (US)

( * ) Notice: Subject to any disclaimer, the term of this patent is extended or adjusted under 35 U.S.C. 154(b) by 0 days.

(21) Appl. No.: 09/564,491

(22) Filed: May 4, 2000

Related U.S. Application Data

(63) Continuation of application No. 09/363,521, filed on Jul. 29, 1999, now abandoned.
(60) Provisional application No. 60/112,023, filed on Jul. 30, 1998.

(51) Int. Cl.[7] .................... C07D 239/94; A01K 31/505; A01R 35/00
(52) U.S. Cl. ...................................... 544/293; 514/259
(58) Field of Search ........................... 544/293; 514/259

(56) References Cited

U.S. PATENT DOCUMENTS

| 5,457,105 A | 10/1995 | Barker ........................ 544/284 |
| 5,760,041 A | 6/1998 | Wissner et al. ............. 544/293 |

FOREIGN PATENT DOCUMENTS

| AU | 3101092 | 7/1993 |
| EP | 0602851 | 6/1994 |
| EP | 0787722 | 6/1997 |
| WO | 9615118 | 5/1996 |
| WO | 9630347 | 10/1996 |

*Primary Examiner*—Richard L. Raymond
*Assistant Examiner*—Venkataraman Balasubramanian
(74) *Attorney, Agent, or Firm*—John W. Hogan, Jr.

(57) ABSTRACT

This invention provides a process for preparing compounds of formula 1:

wherein:
  X is phenyl optionally substituted with one or more substituents selected from the group consisting of halogen, alkyl of 1–6 carbon atoms, alkoxy of 1–6 carbon atoms, hydroxy, trifluoromethyl, cyano, nitro, carboxy, carboalkoxy of 2–7 carbon atoms, carboalkyl of 2–7 carbon atoms, amino, and alkanoylamino of 1–6 carbon atoms;
  R and $R_1$ are each, independently, hydrogen, halogen, alkyl of 1–6 carbon atoms, alkoxy of 1–6 carbon atoms, hydroxy, or trifluoromethyl;
  $R_2$ is hydrogen, alkyl of 1–6 carbon atoms, alkoxy of 1–6 carbon atoms, hydroxy, trifluoromethyl;

Y is $R_3$ is independently hydrogen, alkyl of 1–6 carbon atoms, carboxy, carboalkoxy of 1–6 carbon atoms, phenyl, or carboalkyl of 2–7 carbon atoms;
  n=2–4;
or a pharmaceutically acceptable salt thereof, with the proviso that each $R_3$ of Y may be the same or different.

11 Claims, No Drawings

SUBSTITUTED QUINAZOLINE DERIVATIVES

This application is a continuation of U.S. application Ser. No. 09/363,521 filed Jul. 29, 1999 now abandoned which claims benefit of U.S. Provisional Application No. 60/112,023 filed Jul. 30, 1998.

BACKGROUND OF THE INVENTION

This invention relates to the preparation of certain quinazoline compounds as well as intermediates thereof. The quinazolines prepared by the process of the present invention inhibit the action of certain growth factor receptor protein tyrosine kinases (PTK) thereby inhibiting the abnormal growth of certain cell types. These quinazolines are anti-cancer agents and are useful for the treatment of cancer in mammals.

Protein tyrosine kinases are a class of enzymes that catalyze the transfer of a phosphate group from ATP to a tyrosine residue located on a protein substrate. Protein tyrosine kinases clearly play a role in normal cell growth. Many of the growth factor receptor proteins function as tyrosine kinases and it is by this process that they effect signaling. The interaction of growth factors with these receptors is a necessary event in normal regulation of cell growth. However, under certain conditions, as a result of either mutation or overexpression, these receptors can become deregulated; the result of which is uncontrolled cell proliferation which can lead to tumor growth and ultimately to the disease known as cancer [Wilks A. F., *Adv. Cancer Res.*, 60, 43 (1993) and Parsons, J. T.; Parsons, S. J., *Important Advances in Oncology*, DeVita V. T. Ed., J.B. Lippincott Co., Phila., 3 (1993)]. Among the growth factor receptor kinases and their proto-oncogenes that have been identified and which are targets of the compounds of this invention are the epidermal growth factor receptor kinase (EGF-R kinase, the protein product of the erbB oncogene), and the product produced by the erbB-2 (also referred to as the neu or HER2) oncogene. Since the phosphorylation event is a necessary signal for cell division to occur and since overexpressed or mutated kinases have been associated with cancer, an inhibitor of this event, a protein tyrosine kinase inhibitor, will have therapeutic value for the treatment of cancer and other diseases characterized by uncontrolled or abnormal cell growth. For example, overexpression of the receptor kinase product of the erbB-2 oncogene has been associated with human breast and ovarian cancers [Slamon, D. J., et. al., *Science*, 244, 707 (1989) and *Science*, 235, 1146 (1987)]. Deregulation of EGF-R kinase has been associated with epidermoid tumors [Reiss, M., et. al., *Cancer Res.*, 51, 6254 (1991)], breast tumors [Macias, A., et. al., *Anticancer Res.*, 7, 459 (1987)], and tumors involving other major organs [Gullick, W. J., *Brit. Med. Bull.*, 47, 87 (1991)]. Because the importance of the role played by deregulated receptor kinases in the pathogenesis of cancer, many recent studies have dealt with the development of specific PTK inhibitors as potential anti-cancer therapeutic agents [some recent reviews: Burke. T. R., *Drugs Future*, 17, 119 (1992) and Chang, C. J.; Geahlen, R. L., *J. Nat. Prod.*, 55, 1529 (1992)].

DESCRIPTION OF THE INVENTION

This invention provides a process for preparing a compound of formula 1:

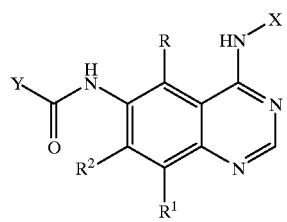

wherein:

X is phenyl optionally substituted with one or more substituents selected from the group consisting of halogen, alkyl of 1–6 carbon atoms, alkoxy of 1–6 carbon atoms, hydroxy, trifluoromethyl, cyano, nitro, carboxy, carboalkoxy of 2–7 carbon atoms, carboalkyl of 2–7 carbon atoms, amino, and alkanoylamino of 1–6 carbon atoms;

R and $R_1$ are each, independently, hydrogen, halogen, alkyl of 1–6 carbon atoms, alkoxy of 1–6 carbon atoms, hydroxy, or trifluoromethyl;

$R_2$ is hydrogen, alkyl of 1–6 carbon atoms, alkoxy of 1–6 carbon atoms, hydroxy, trifluoromethyl;

Y is

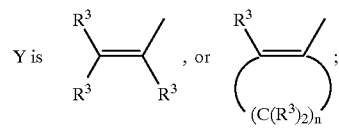

$R_3$ is independently hydrogen, alkyl of 1–6 carbon atoms, carboxy, carboalkoxy of 1–6 carbon atoms, phenyl, or carboalkyl of 2–7 carbon atoms;

n=2–4;

or a pharmaceutically acceptable salt thereof, with the proviso that each $R_3$ of Y may be the same or different, which comprises:

a) acylating a compound of the formula:

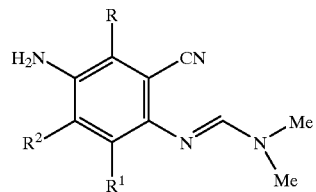

with an acid chloride or mixed anhydride having the formula:

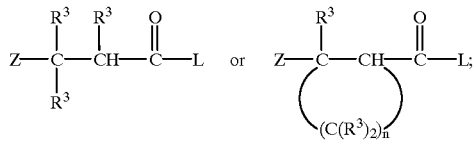

wherein

Z is —$OR^4$, —$SR^4$, —$SOR^4$, —$SO_2R^4$, halogen, —$NHR^5$, or —$NR^5R^5$;

$R^4$ is all of 1–6 carbon atoms, cycloalkyl of 3–8 carbon atoms, or phenyl;

$R^5$ is alkyl of 1–6 carbon atoms or cycloalkyl of 3–8 carbon atoms;

L is Cl, Br, or —OC(O)$R^6$;

$R^6$ is alkyl of 1–6 carbon atoms, cycloalkyl of 3–8 carbon atoms, or phenyl;

$R^3$ and n are as defined above;

b) reacting the acylated product of step a) with $H_2N$—X, wherein

X is as defined above; and c) treating the compound of step b) with a mild base to give the compound of Formula 1.

The preparation of compounds of Formula 1 and use as antineoplastic agents have been disclosed in U.S. Pat. No. 5,760,041, which is hereby incorporated by reference. The processes described herein provide a new method of preparing these compounds which does not produce polymerization of the vinyl moiety (of the compounds Formula 1), which occurred using the procedures described in U.S. Pat. No. 5,760,041.

The alkyl moieties described herein include both straight chain as well as branched carbon chains. Carboxy is defined as a —$CO_2H$ radical. Carboalkoxy of 2–7 carbon atoms is defined as a —$CO_2R''$ radical, where R" is an alkyl radical of 1–6 carbon atoms. Carboalkyl is defined as a —COR" radical, where R" is an alkyl radical of 1–6 carbon atoms. When X is substituted, it is preferred that it is mono-, di-, or tri-substituted, with monosubstituted being most preferred. When a compound produced by the processes of this invention contains an assymetric center, this invention covers the individual R and S entantiomers as well as the racemate with respect to such compound. The pharmaceutically acceptable salts of compounds of Formula 1 are those derived from such organic and inorganic acids as: acetic, lactic, citric, tartaric, succinic, maleic, malonic, gluconic, hydrochloric, hydrobromic, phosphoric, nitric, sulfuric, methanesulfonic, and similarly known acceptable acids. The pharmaceutically acceptable salts can be prepared from the corresponding free base compounds using standard chemical methodology.

Of the compounds of this invention, preferred members include those in which R, $R^1$, and $R^2$ are hydrogen; and those in which R, $R^1$, and $R^2$ are hydrogen and X is either unsubstituted or monosubstituted with halogen or alkyl of 1–6 carbon atoms. Preferred Z moieties include —$OR^4$, —$SR^4$, —$SOR^4$, —$SO_2R^4$, halogen, where $R^4$ is alkyl of 1–6 carbon atoms. It is also preferred that the acylating agent has the formula:

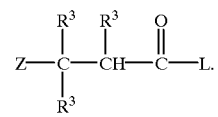

The following scheme illustrates the preparation of compounds of Formula 1; the preferred acylating agent is exemplified in this scheme. The starting materials used in this synthesis are either commercially available or can be prepared using standard chemical methodology. For example, the starting imino aniline can be prepared from the nitrophenyl imine disclosed in U.S. Pat. No. 5,760,041.

Scheme I

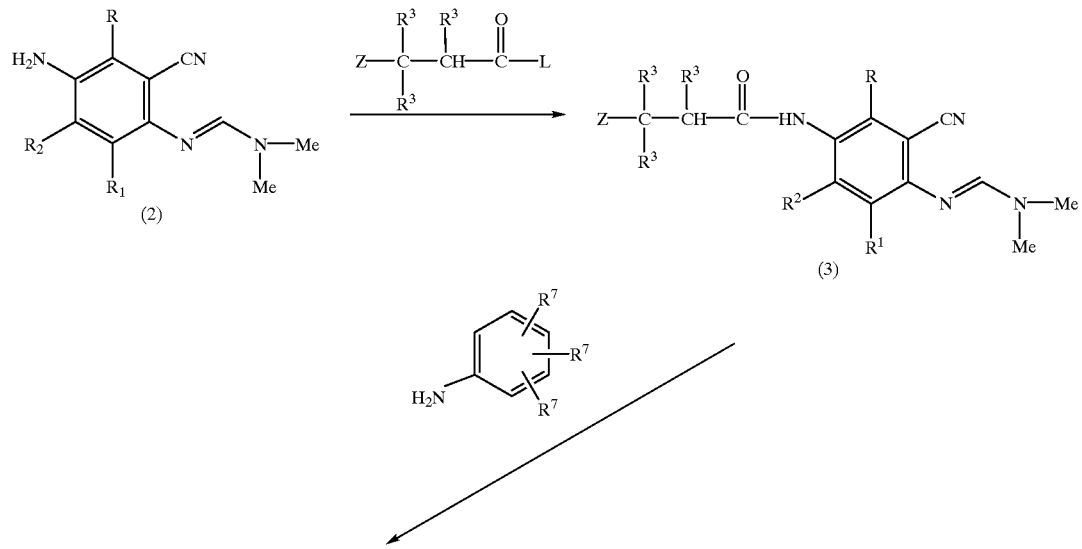

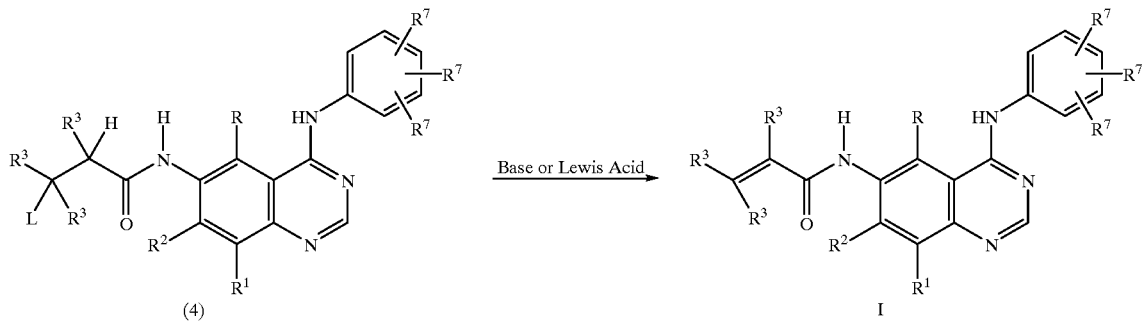

The acylating agent in the first step can either be an acid halide or can be a mixed anhydride. When the acylating agent is a mixed anhydride, the mixed anhydride can either be prepared as a separate step, or more preferably made in situ. The acylation reaction is typically carried out in the presence of a mild base, such as N-methyl morpholine, diisopropyl ethylamine, pyridine, and triethylamine.

In the second step, a Dimroth type rearrangement [Synthesis, 851(1988); Heterocyclic Chem., 16, 33(1974); Tetrahedron, 28, 535(1972); Z. Chem., 9, 241(1969)] can be carried out using a suitable solvent such as acetic acid, water, monohydric alcohols such as ethanol or isopropyl alcohol, or DMF, at temperatures ranging from ambient temperature to reflux. It is preferred that the reaction be carried out at temperatures above 78° C. Acetic acid at reflux were found to be the preferred conditions to effect this transformation.

Elimination of HL to provide compounds of Formula 1 could be accomplished under mild conditions which prevented polymerization of the final product using bases such as potassium ethoxide, potassium t-butoxide, primary, secondary, or tertiary alkoxide bases, or sodium carbonate in solvents such as ethanol, DMF, DMSO, THF, dioxane, methyl t-butyl ether, or diisopropyl ether. Acceptable reaction temperatures ranged from ambient to reflux. It is preferred that the elimination reaction be carried out using potassium t-butoxide in DMF at ambient temperature. It also preferred that at least three molar equivalents of base be used in this reaction. Alternatively, the elimination reaction could be accomplished using Lewis Acids such as $ZnCl_2$, $nBu_4NF$, $CuSO_4$, $BF_3.Et_2O$, or $Yb(OTf)_3$ in solvents such as nitrobenzene, nitromethane, carbon disulfide, or chlorinated hydrocarbons, such as dicloromethane or chloroform.

Scheme II shows the preparation of 4-(3-bromophenylamine)-6-(vinylamide)quinazoline), a representative compound of Formula 1, using the methodology described above. The preparation and antineoplastic activity of 4-(3-bromophenylamine)-6-(vinylamide)quinazoline) were disclosed in U.S. Pat. No. 5,760,041.

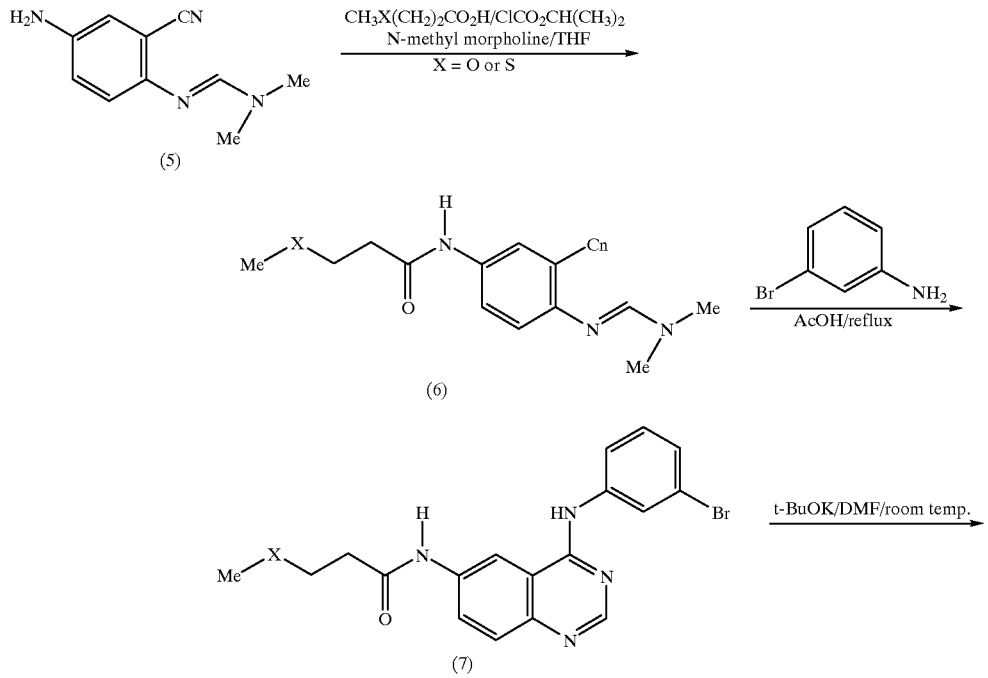

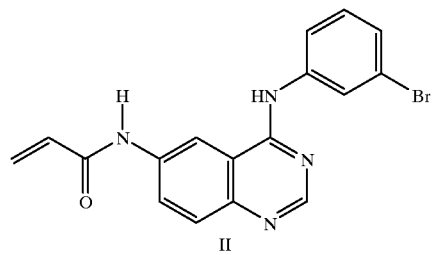

II

The first two steps of Scheme 2 can also be carried out as a one pot synthesis where X is O or S, thereby eliminating the need for isolation of compound (6).

Alternatively, 4-(3-bromophenylamine)-6-(vinylamide) quinazoline) was prepared by converting the methyl sulfide (7) the corresponding sulfoxide (12) or sulfone (13), followed by mild basic elimination of the better leaving group. Conversion to the sulfoxide was accomplished with one mole of m-chloroperbenzoic acid in THF/DMF at −50° C. to ambient temperature. Other oxidants such as hydrogen peroxide and Caro's acid also provided satisfactory results. The corresponding sulfone was prepared from the methyl sulfide using OXONE (potassium peroxymonosulfate) in THF/methanol/water. The sulfone was also prepared using at least two molar equivalents of other oxidizing agents such as hydrogen peroxide, chlorine, ozone, or m-chloroperbenzoic acid. As 4-(3-bromophenylamine)-6-(vinylarnide) quinazoline) is useful as an antineoplastic agent, the compounds of Examples 1, 2, 4, 5, 7, 8, and 9 are useful as intermediates in its preparation.

The preparation of representative examples of the compounds covered by the process of this invention are described below.

EXAMPLE 1

1-(3-Methoxy Propionyl)-3-cyano-4-(dimethyl Formamidyl)aniline (6, X=O)

A solution of 3-methoxy propionic acid (1.30 g, 12 mmol) and isobutyl chloroformate (1.56 g, 12 mmol) in THF (20 mL) was stirred and cooled to 0° C. To it were added dropwise over 30 min., a solution of N-methylmorpholine (1.21 g, 12 mmol) in THF (5 mL), while the temperature was maintained at 0–5° C. The reaction mixture was stirred at 0–5° C. for another 15 min. and then to it was added over 30 min., a pre-made solution, prepared as follows: 3-cyano4-(dimethylformamidyl)aniline (5) (2.26 g, 12 mmol) and N-methylmorpholine (1.21 g, 12 mmol) in THF (20 mL). This was a slurry and it had to be warmed to 35° C. to effect solubilization, before use. This solution maintained its clarity after cooling to 20–25° C., before and during its addition. During the addition, the reaction temperature was maintained at 0–5° C.

After the addition, the reaction mixture was stirred at 0–5° C. for 30 min.; the cooling was removed and the resulting slurry was stirred at 20–25° C. for another 2.5 hrs. An aqueous sodium chloride solution (20 mL, 20%) was added, the layers separated and the organic layer concentrated to provide an oil. Toluene (50 mL) was added to the oil and the mixture azeotroped in vacuo twice. Additional toluene (50 mL) was added and the mixture stirred, while cooling to 0–5° C., the temperature was maintained at 0–5° C. until crystallization is established. The white solid was filtered and washed with toluene (3×5 mL) and hexanes (1×10 mL). The product was dried in a vacuum oven at 60° C. A single crop of the title compound of 3.10 g (94.2%) was obtained; m.p. 143–145° C.

TLC (dichloromethane-5% methanol) showed a single spot at $R_f$ 0.36; $^1$H NMR (300 MHz, DMSO-$d_6$) 2.52 (t, J=6 Hz, 2H, $CH_2$—C=O), 2.97 (s, 3H, $CH_3$—N), 3.05 (s, 3H, $CH_3$—N), 3.24 (s, 3H, $CH_3O$—), 3.61 (t, J=6 Hz, 2H, —$CH_2$—O), 7.90 (s, 1H, N=CH—N amidine), 7.1–8.0 (m, 3H, Ar—H), 10.05 (s, 1H, NH, amide).

EXAMPLE 2

4-(3-Bromo Phenyl Amine)-6-(3-methoxy Propionyl Amide)-quinazoline (7; X=O)

{Direct Method from (5), Without Isolation of (6; X=O)}

A solution of 3-methoxy propionic acid (1.30 g, 12 mmol) and isobutyl chloroformate (1.56 g, 12 mmol) in THF 20 mL) was stirred and cooled to 0° C. To it was added, a solution of N-methylmorpholine (1.21 g, 12 mmol) in THF (5 mL), dropwise over 30 min. while maintaining 0–5° C. The mixture was stirred at 0–5° C. for another 15 min. and then add to was added over 30 min., a pre-made solution prepared as follows: 3-cyano-4-(dimethylformamidyl) aniline (5) (2.26 g, 12 mmol) and N-methylmorpholine (1.21 g, 12 mmol) in THF (20 mL). This was a slurry and had to be warmed to 35° C. to effect solubilization, before use. This solution maintained its clarity after cooling to 20–25° C., before and during its addition. During the addition, the reaction temperature was maintained at 0–5° C.

After the addition, the mixture was stirred at 0–5° C. for 30 min., the cooling, was removed, and the slurry was stirred at 20–25° C. for another 2.5 hrs. To it was added an aqueous sodium chloride solution (20%), the layers were separated and the organic layer concentrated in vacuo to an oil. Glacial acetic acid (15 mL) and 3-bromo aniline (2.29 g, 13.3 mmol) were added, and the mixture refluxed (114–116° C.) for 1.25 hrs.

The reaction mixture was concentrated in vacuo to a small volume (about 10 mL) and acetonitrile (30 mL) added. The mixture was heated to bring the oil into solution (about 60° C.) and then cooled slowly with slow stirring to induce crystallization (crystallization started at about 45° C.). The mixture was stirred at 20–25° C. for one hour, cooled to 0–5° C. and maintained for at least one additional hour. The solids were filtered and washed the with acetonitrile (4×2 mL) and dried in a vacuum oven at 60° C. to give 3.03 g (63.0%) of the title material as first crop; m.p. 216–218° C.; TLC and $^1$H NMR shown below.

A second crop was obtained by basifying the filtrates with an aqueous sodium carbonate solution (20 mL, 20%), extracting with dichloromethane (2×20 mL), washing to neutrality with water (2×10 mL). The combined organic layers were concentrated under vacuum and azeotroped with toluene (2×20 mL) to a final volume (about 10 mL). Crystallization was initiated by stirring at 20–25° C. for at least one hour. The crystals were collected by filtration, washed with toluene (2×2 mL), hexanes (2×2 mL) and dried in a vacuum oven at 60° C. to give the title compound as a white solid (1.25 g; 26.1%), which was identical to the first crop; m.p. 216–218° C.; TLC and $^1$H NMR are shown below. Overall yield 4.28 g (89.1%).

TLC (dichloromethane-5% methanol) showed a single spot at $R_f$ 0.24; $^1$H NMR (300 MHz, DMSO-d$_6$) 2.65 (t, J=6 Hz, 2H, CH$_2$C=O), 3.28 (s, 3H, CH$_3$O—), 3.68 (t, J=6 Hz, 2H, —CH$_2$O—), 7.20–8.80 (m, 8H, Ar—H), 9.95 (s, 1H, NH, amide), 10.35 (s, 1H, NH, amine).

EXAMPLE 3

4-(3-Bromo Phenyl Amine)-6-(vinyl Amide) quinazoline (II) from (7, X=O)

To a solution of 4-(3-bromo phenyl amine)-6-(3-methoxy propionyl amide) quinazoline (7, X=O) (0.201 g, 0.5 mmol) in dimethyl formamide (2.5 mL), was added potassium tert-butoxide (0.178 g, 1.5 mmol). The mixture was stirred at ambient temperature for five hours, preferably overnight, until the reaction was completed (TLC/HPLC). A darkening and a small exotherm (34° C.) observed initially upon the base addition.

The mixture was partition between ethyl acetate (10 ml) and aqueous sodium chloride (10 mL, 20%). The layers were separated and the organic layer extracted to neutrality with aqueous sodium chloride (3×10 mL, 20%), dried over anhydrous magnesium sulfate (1.5 g) for at least one hour, and the slurry filtered over a plug of silica gel (3 g). The silica gel plug was washed with a solution of ethyl acetate-10% methanol (20 mL–2 mL), and the combined filtrates concentrated under vacuum to a yellow solid (0.200 g). Ethyl ether (5 mL) was added and the mixture stirred for one hour, filtered, and the solid washed with ethyl ether (2×0.5 mL) and dried under vacuum (60° C.) to provide the title compound as a light yellow solid, 0.154 g (83.4%); m.p. 288–290° C.(dec.).

TLC (dichloromethane-5% methanol) showed one single spot at $R_f$ 0.40, identical to authentic;

$^1$H NMR (300 MHz, DMSO-d$_6$) 5.85 (d, J$_{cis}$=11 Hz, 1H, C=CH geminal vinyl), 6.35 (d, J$_{trans}$=15 Hz, 1H, C=CH geminal vinyl), 6.54 (q, J$_{trans}$=10 Hz, J$_{cis}$=7 Hz, 1H, C=CH—C=O— vicinal vinyl), 7.20–8.90 (m, 8H, Ar—H), 9.94 (s, 1H, NH amide), 10.55 (s, 1H, NH amine).

EXAMPLE 4

1-(3-Methylthio Propionyl)-3-cyano-4-(dimethyl Formamidyl)aniline (6; X=S)

A solution of 3-methylthio-propionic acid (2.00 g, 16.5 mmol) and isobutyl chloroformate (2.20 g, 16.5 mmol) in THF 25 mL) was stirred and cooled to 0° C. To it was added dropwise over 30 min., a of solution of N-methylmorpholine (1.70 g, 16.5 mmol) in THF (5 mL), while maintaining a temperature of 0–5° C. The mixture was stirred at 0–5° C. for another 15 min. and then over 30 min., was added a pre-made solution, prepared as follows: 3-cyano-4-(dimethylformamidyl)aniline (4) (3.10 g, 16.5 mmol) and N-methylmorpholine (1.70 g, 16.5 mmol) in THF (25 mL). This was a slurry and it had to be warmed to 35° C. to effect solubilization, before use. This solution maintained its clarity after cooling to 20–25° C., before and during its addition. During the addition, the reaction mixture was maintained at 0–5° C.

After the addition the mixture was stirred at 0–5° C. for 30 min.; the cooling was removed, and the slurry was stirred at 20–25° C. for another 2.5 hrs. An aqueous sodium chloride solution (25 mL, 20%) was added; the layers were separated and the organic layer concentrated in vacuo to an oil. Toluene (50 mL) was added to the oil and the mixture azeotroped in vacuo twice. Toluene (50 mL) was added to the glassy semi-solids; the mixture was heated to 60° C. and stirred for 15 min. The mixture was cooled to 20–25° C. and stirred for 0.5 hr., then cooled to 0–5° C., and stirred for an additional 0.5 hr. The white solid was filtered and washed with toluene (3×10 mL) and hexanes (2×10 mL). The product was dried in a vacuum oven at 60° C. A single crop of the title compound (3.80 g; 79.3%); m.p. 196–198° C.(dec.) was obtained.

TLC (dichloromethane-5% methanol) showed a single spot at $R_f$ 0.48; $^1$H NMR (300 MHz, DMSO-O$_6$) 2.09 (s, 3H, CH$_3$S—), 2.60 (t, J=7 Hz, 2H, CH$_2$—C=O), 2.74 (t, J=7 Hz, 2H, —CH$_2$—S), 2.98 (s, 3H, CH$_3$—N), 3.06 (s, 3H, CH$_3$—N), 7.93 (s, 1H, N=CH—N amidine), 7.1–8.0 (m, 3H, Ar—H), 10.13 (s, 1H, NH, amide).

EXAMPLE 5

4-(3-Bromo Phenyl Amine)-6-(3-methylthio Propionyl Amide)quinazoline (7; X=S)
{Direct Method from (5), Without Isolation of (6; X=S)}

A solution of 3-methylthio-propionic acid (2.00 g, 16.5 mmol) and isobutyl chloroformate (2.20 g, 16.5 mmol) in THF 25 mL) was stirred and cooled to 0° C. To it was added a solution of N-methylmorpholine (1.70 g, 16.5 mmol) in THF (5 mL), dropwise over 30 min. while maintaining 0–5° C. The mixture was stirred at 0–5° C. for another 15 min. and then the following solution was added to it over 30 min, while maintaining a reaction temperature of 0–5° C.: 3-cyano-4-(dimethylformamidyl)aniline (5) (3.10 g, 16.5 mmol) and N-methylmorpholine (1.70 g, 16.5 mmol) in THF (25 mL). This was a slurry and it had to be warmed to 35° C. to effect solubilization, before use. This solution maintained its clarity after cooling to 20–25° C., before and during its addition.

After the addition the mixture was stirred at 0–5° C. for 30 min.; the cooling was removed and the slurry was stirred at 20–25° C. for another 2.5 hrs. An aqueous sodium chloride solution (25 mL, 20%) was added and the organic layer was separated and placed in a new flask. Glacial acetic acid (20 mL) was added to the organic layer, and the mixture concentrated under vacuum to a small volume (about 10 mL). To this syrupy solution was added glacial acetic acid (10 mL), 3-bromo aniline (3.10 g, 18.1 mmol), and the reaction mixture refluxed (114–116° C.) for 1.5 hr.

The clear solution was cooled to 20–25° C. and acetonitrile (40 mL) added. Crystallization started after cooling to 0–5° C. The mixture was cooled for an additional hour at 0–5° C. The white solid was filtered, washed with acetonitrile (3×5 mL) and dried under vacuum (60° C.) to provide 4.38 g (63.6%) of the title compound, as a first crop; m.p. 236–239° C.; TLC and $^1$H NMR are shown below.

A second crop was obtained by concentrating the filtrates to a small volume (about 10 mL), adding acetonitrile (40 mL), stirring at 20–25° C. for at least one hour and then at 0–5° C. for another hour. The resulting white solid was filtered, washed with acetonitrile (3×10 mL) and dried in the vacuum oven (60° C.) to provide 2.40 g (34.9%) as second crop, which was identical to the title compound; m.p. 236–239° C. Overall yield 6.78 g (98.5%).

TLC (dichloromethane-5% methanol) showed a single spot at $R_f$ 0.20; $^1$H NMR (300 MHz, DMSO-d$_6$) 2.12 (s, 3H, CH$_3$S—), 2.72 (t, J=6.5 Hz, 2H, CH$_2$C=O), 2.81 (t, J=6.5 Hz, 2H, —CH$_2$O—), 7.20–8.80 (m, 8H, Ar—H), 9.95 (s, 1H, NH, amide), 10.45 s, 1H, NH, amine).

EXAMPLE 6

4-(3-Bromo Phenyl Amine)-6-(vinyl Amide) quinazoline (II) from (7; X=S)

To a solution of 4-(3-bromo phenyl amine)-6-(3-methylthio propionyl amide)quinazoline (7, X=S) (0.208 g, 0.5 mmol) in dimethyl formamide (2.5 mL), was added potassium tert-butoxide (0.178 g, 1.5 mmol) and the mixture was stirred at ambient temperature. A darkening and a small exotherm (34° C.) was observed initially upon the base addition. The reaction was progressing slowly at ambient temperature and it was not completed (TLC/HPLC) after two days.

The reaction mixture was partitioned between ethyl acetate (10 mL)/aqueous sodium chloride (10 mL, 20%). The layers were separated and the organic layer was extracted to neutrality with aqueous sodium chloride (3×10 mL, 20%). The organic layer was dried over anhydrous magnesium sulfate (1.5 g) for at least one hour and filtered over a plug of silica gel (3 g). The silica plug was washed with a solution of ethyl acetate-10% methanol (20 mL–2 mL). The filtrate was concentrated under vacuum to a yellow solid (0.184 g) and added to ethyl ether (5 mL). The mixture was stirred for one hour, filtered; the solid was washed with ethyl ether (2×0.5 mL) and dried under vacuum (60° C.). The light yellow solid, 0.150 g (81.2%) was a mixture of 50.5% the title compound (II) and 38.0% starting material (7, X=S) by HPLC. This was confirmed by TLC (dichloromethane-5% methanol) which showed two spots in a 50/40 ratio of (1)/(11) respectively. The $^1$H NMR (300 MHz, DMSO-d$_6$) indicated the same ratio 5/4 of the characteristic frequencies of both compounds (II) and (7) respectively.

EXAMPLE 7

1-(3-Chloro Propionyl)-3-cyano-4-(dimethyl Formamidyl)aniline (Scheme I; 3, Z=Cl)

3-cyan-4-(dimethylformamidyl)aniline (5) (3.10 g, 16.5 mmol) and N-methylmorpholine (1.70 g, 16.5 mmol) was stirred in THF (25 mL). The mixture was a slurry and had to be warmed to 35° C. to effect solubilization. This solution lost its clarity after cooling and was maintained at 0–5° C. as a slurry.

To the above slurry was added very slowly, over 1.25 hr., a solution of 3-chloro-propionic acid (2.10 g, 16.5 mmol) in THF (10 mL). The reaction was maintained at 0–5° C.; and stirred at that temperature for an additional half an hour. An aqueous sodium chloride solution (25 mL, 20%) was added, the layers separated and the organic layer concentrated in vacuo to a solid. Toluene (50 mL) was added to this solid and the mixture azeotroped in vacuo twice. Toluene (50 mL) was again added and the mixture heated to 60° C., and stirred for 15 min. The mixture was cooled to 20–25° C., stirred for 0.5 hr., then cooled to 0–5° C., and stirred for an additional 0.5 hr. The resulting white solid was filtered and washed with toluene (2×25 mL) and ethyl ether (2×25 mL). The product was dried in a vacuum oven at 60° C. A single crop of the title compound of 4.40 g (95.7%) was obtained; m.p. 174–175° C.

TLC (dichloromethane-5% methanol) showed a single spot at R$_f$ 0.44; $^1$H NMR (300 MHz, DMSO-d$_6$) 2.81 (t, J=6 Hz, 2H, CH$_2$—C=O), 3.88 (t, J=6 Hz, 2H, —CH$_2$—Cl), 2.98 (s, 3H, CH$_3$—N), 3.06 (s, 3H, CH$_3$—N), 7.92 (s, 1H, N=CH—N amidine), 7.1–8.0 (m, 3H, Ar—H), 10.20 (s, 1H, NH, amide).

EXAMPLE 8

4-(3-Bromo Phenyl Amine)-6-(3-methylsulfoxido Proplonyl Amide)-quinazoline (12), from (7; X=S)

A solution of 4-(3-bromo phenyl amine)-6-(3-methylthio propionyl amine)-quinazoline (7; X=S, 0.208 g, 0.5 mmol), THF (2 mL) and DMSO (0.25 mL) was cooled to −50° C. A solution of m-chloroperbenzoic acid (0.110 g, 0.5 mmol) in THF (1 mL) was added over one minute, keeping −40 to −50° C. The reaction mixture was stirred at −50° C. for 30 minutes; the cooling removed and the mixture was allowed to warm to 20–25° C.

The reaction mixture was partitioned between ethyl acetate (10 mL) and aqueous NaCl (10 mL, 20%). The organic layer was separated and extracted to neutrality with aqueous NaCl (3×10 mL) and water (1×10 mL).The organic layer was dried with MgSO$_4$ (1 g), filter, washed with ethyl acetate (3×2 mL) and concentrated under vacuum to a gray solid, which was triturated with acetonitrile (3 mL) by heating to 70° C. and then cooling to 20–25° C. The solid was filtered, washed with acetonitrile (3×0.5 mL) and dried in a vacuum oven (60° C.). White solid identical to title compound (12) 0.203 g (93.8%); m.p. 286–288° C. (dec.).

TLC (dichloromethane-5% methanol) showed a single spot at R$_f$ 0.10; $^1$H NMR (300 MHz, DMSO-d$_6$) 2.61 (s, 3H, CH$_3$SO—), 2.88 (m, 2H, CH$_2$C=O), 3.16 (m, 2H, —CH$_2$S=O), 7.20–8.80 (m, 8H, Ar—H), 9.94 (s, 1H, NH, amide), 10.49 (s, 1H, NH, amine).

EXAMPLE 9

4-(3-Bromo Phenyl Amine)-6-(3-methylsulfono Propionyl Amide)-quinazoline (13), from (7; X=S)

To a solution of 4-(3-bromo phenyl amine)-6-(3-methylthio propionyl amine)-quinazoline (11; X=S, 0.208 g, 0.5 mmol), THF (2 ML) and MeOH (1 mL) cooled to 0° C., was added add a solution of OXONE (0.616 g, 1 mmol) in water (2 mL) over one minute, keeping the reaction temperature at 0–5° C. The mixture was stirred at 0–5° C. for 4.5 hours; the cooling was removed and the reaction allowed to warm to 20–25° C.

The reaction mixture was partitioned between ethyl acetate (10 mL) and aqueous Na$_2$CO$_3$ (10 mL, 20%) resulting in an emulsion. The emulsion was diluted with aqueous NaCl (20 mL, 20%) and filtered. The solids were slurried and washed on a filter funnel with water (3×10 mL) and ethyl acetate (2×2 mL). The product was dried in a vacuum oven (60° C.). White solid consistent to tide compound(13) 0.148 g (65.9%); m.p. 248–250° C.(dec.).

TLC (dichloromethane-5% methanol) showed a single spot at R$_f$ 0.36; $^1$H NMR (300 MHz, DMSO-d$_6$) 2.92 (t, J=7.5 Hz, 2H, CH$_2$C=O), 3.07 (s, 3H, CH$_3$SO$_2$—), 3.45 (t, J=7.5 Hz, 2H, —CH$_2$SO$_2$), 7.20–8.80 (m, 8H, Ar—H), 9.95 (s, 1H, NH, amide), 10.49 (s, 1H, NH, amine).

EXAMPLE 10

4-(3-Bromo Phenyl Amine)-6-(3-methylsulfono Propionyl Amide)quinazoline (13), from (12)

To a solution of 4-(3-bromo phenyl amine)-6-(3-methysulfoxido propionyl amine)quinazoline (12, 0.216 g, 0.5 mmol), THF (3 mL), MeOH (2 mL) and DMF (2 mL) at 0° C., was added add a solution of OXONE (0.616 g, 1 mmol) in water (2 mL) over one minute, while maintaining the temperature at 0–5° C. The mixture was stirred at 0–5° C. for 0.5 hr. and at 20–25° C. for 2.5 hrs.

The reaction mixture was partitioned between ethyl acetate (10 mL) and aqueous $Na_2CO_3$ (10 mL, 20%). An emulsion resulted. The emulsion was diluted with aqueous NaCl (20 mL, 20%) and filtered. The solids were slurried and washed on a filter with water (2×2.5 mL) and ethyl acetate (2×2.5 mL). The product was dried in a vacuum oven (60° C.). The resulting white solid was consistent to tide compound (13) 0.50 g (67.0%); m.p. 248–250° C.(dec.).

TLC (dichloromethane-5% methanol) showed a single spot at $R_f$ 0.36; $^1$H NMR (300 MHz, DMSO-$d_6$) 2.92 (t, J=7.5 Hz, 2H, $CH_2C$=O), 3.07 (s, 3H, $CH_3SO_2$—), 3.45 (t, J=7.5 Hz, 2H, —$CH_2SO_2$), 7.20–8.80 (m, 8H, Ar—H), 9.95 (s, 1H, NH, amide), 10.49 s, 1H, NH, amine).

EXAMPLE 11

4-(3-Bromo Phenyl Amine)-6-(vinyl Amide) quinazoline (II) from (12)

To a solution of 4-(3-bromo phenyl amine)-6-(3-methylsulfoxido propionyl amide)quinazoline (12) (0.043 g, 0.1 mmol) in DMF (2 mL), was added potassium tert-butoxide (0.035 g, 0.3 mmol). The reaction mixture was stirred at ambient temperature for one hour, whereupon the reaction was completed (TLC/HPLC). A darkening, but no exotherm was observed initially upon the base addition.

The reaction mixture was partitioned between ethyl acetate (10 mL) and aqueous sodium chloride (10 mL, 20%). The layers were separated, the organic layer extracted to neutrality with aqueous sodium chloride (3×10 mL, 20%), dried over anhydrous magnesium sulfate (1.5 g) for at least one hour, and filtered over a plug of silica gel (3 g). The plug was washed with a solution of ethyl acetate-10% methanol (20 mL–2 mL). The filtrates were concentrated under vacuum to a yellow solid (0.025 g). Ethyl ether (3 mL) was added, the mixture stirred for one hour, filtered, washed with ethyl ether (3×0.5 mL) and dried it under vacuum (60° C.). The resulting light yellow solid, 0.020 g (55.0%) was identical to the title compound (II); m.p. 288–290° C.(dec.).

TLC (dichloromethane-5% methanol) showed one single spot at $R_f$ 0.40, identical to authentic;

$^1$H NMR (300 MHz, DMSO-$d_6$) 5.85 (d, $J_{cis}$=11 Hz, 1H, C=CH geminal vinyl), 6.35 (d, $J_{trans}$=15 Hz, 1H, C=CH geminal vinyl), 6.54 (q, $J_{trans}$=10 Hz, $J_{cis}$=7 Hz, 1H, C=CH—C=O— vicinal vinyl), 7.20–8.90 (m, 8H, Ar—H), 9.94 (s, 1H, NH amide), 10.55 (s, 1H, NH amine).

EXAMPLE 12

4-(3-Bromo Phenyl Amine)-6-(vinyl Amide) quinazoline (II), from (13)

To a solution of 4-(3-bromo phenyl amine)-6-(3-methylsulfono propionyl amide)quinazoline (13) (0.090 g, 0.1 mmol) in DMF (1.5 mL), was added potassium tert-butoxide (0.035 g, 0.3 mmol). The reaction mixture was stirred at ambient temperature for 2 hours, whereupon the reaction was completed (TLC/HPLC). A darkening and a slight exotherm (22 to 24° C.) was observed initially upon the base addition.

The mixture was partitioned between ethyl acetate (10 mL) and aqueous sodium chloride (10 mL, 20%). The layers were separated; the organic layer extracted to neutrality with aqueous sodium chloride (3×10mL, 20%), dried over anhydrous magnesium sulfate (1.5 g) for at least one hour and filtered over a plug of silica gel (3 g). The plug was washed with a solution of ethyl acetate-10% methanol (20 mL–2 mL). The combined filtrates were concentrated under vacuum to a yellow solid (0.075 g) which was added to it ethyl ether (3 mL), stirred for one hour, filtered, washed with ethyl ether (3×0.5 mL) and dried under vacuum (60° C.). The light yellow solid, 0.055 g (74.3%) was identical to the title compound (1); m.p. 288–290° C.(dec.).

TLC (dichloromethane-5% methanol) showed one single spot at $R_f$ 0.40, identical to authentic;

$^1$H NMR (300 MHz, DMSO-$d_6$) 5.85 (d, $J_{cis}$=11 Hz, 1H, C=CH geminal vinyl), 6.35 (d, $J_{trans}$=15 Hz, 1H, C=CH geminal vinyl), 6.54 (q, $J_{trans}$=10 Hz, $J_{cis}$=7 Hz, 1H, C=CH—C=O— vicinal vinyl), 7.20–8.90 (m, 8H, Ar—H), 9.94 (s, 1H, NH amide), 10.55 (s, 1H, NH amine).

I claim:

1. A process for preparing a compound of formula 1:

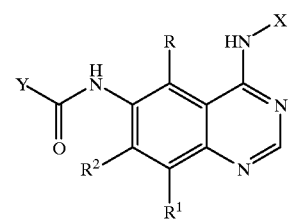

wherein:

X is phenyl optionally substituted with one or more substituents selected from the group consisting of halogen, alkyl of 1–6 carbon atoms, alkoxy of 1–6 carbon atoms, hydroxy, trifluoromethyl, cyano, nitro, carboxy, carboalkoxy of 2–7 carbon atoms, carboalkyl of 2–7 carbon atoms, amino, and alkanoylamino of 1–6 carbon atoms;

R and $R_1$ are each, independently, hydrogen, halogen, alkyl of 1–6 carbon atoms, alkoxy of 1–6 carbon atoms, hydroxy, or trifluoromethyl;

$R_2$ is hydrogen, alkyl of 1–6 carbon atoms, alkoxy of 1–6 carbon atoms, hydroxy, trifluoromethyl;

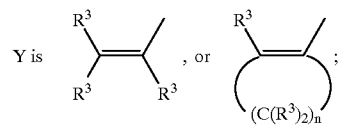

$R_3$ is independently hydrogen, alkyl of 1–6 carbon atoms, carboxy, carboalkoxy of 1–6 carbon atoms, phenyl, or carboalkyl of 2–7 carbon atoms;

n=2–4;

or a pharmaceutically acceptable salt thereof, with the proviso that each $R_3$ of Y may be the same or different, which comprises:

a) acylating a compound of the formula:

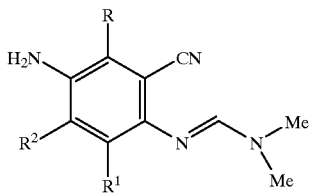

with an acid chloride or mixed anhydride having the formula:

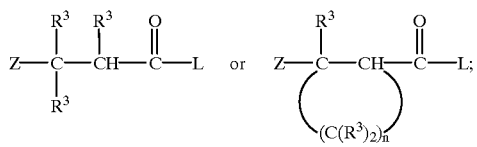

wherein

Z is —OR⁴, —SR⁴, —SOR⁴, —SO₂R⁴, halogen, —NHR⁵, or —NR⁵R⁵;

$R^4$ is alkyl of 1–6 carbon atoms, cycloalkyl of 3–8 carbon atoms, or phenyl;

$R^5$ is alkyl of 1–6 carbon atoms or cycloalkyl of 3–8 carbon atoms;

L is Cl, Br, or —OC(O)R⁶;

$R^6$ is alkyl of 1–6 carbon atoms, cycloalkyl of 3–8 carbon atoms, or phenyl;

$R^3$ and n are as defined above;

b) reacting the acylated product of step a) with H₂N—X, wherein

X is as defined above; and c) treating the compound of step b) with a mild base to give the compound of Formula 1.

2. The process according to claim 1 wherein the acylating agent of step a) is

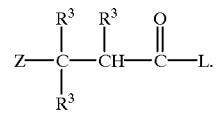

3. The process according to claim 2, wherein R, $R^1$, and $R^2$ are hydrogen.

4. The process according to claim 3, wherein X is either unsubstituted or is monosubstituted with halogen or alkyl of 1–6 carbon atoms.

5. The process according to claim 4, wherein Z is —OR⁴, —SR⁴, —SOR⁴, —SO₂R⁴, halogen and $R^4$ is alkyl of 1–6 carbon atoms.

6. A compound which is selected from the group consisting of 1-(3-methoxy propionyl)-3-cyano-4-(dimethyl formamidyl)aniline; 1-(3-methylthio propionyl)-3-cyano-4-(dimethyl formamidyl)aniline; and 1-(3-chloro propionyl)-3-cyano-4-(dimethyl formamidyl)aniline.

7. The process according to claim 1, wherein said base is selected from the group consisting of potassium ethoxide, potassium t-butoxide, primary, secondary and tertiary alkoxide bases, and sodium carbonate.

8. The process according to claim 7, wherein said step c) is carried out in the presence of a solvent selected from the group consisting of dimethylformamide (DMF), dimethylsulfoxide (DMSO), tetrahydrofuran (THF), dioxane, methyl t-butyl ether and diisopropyl ether.

9. The process according to claim 8, wherein said step c) is carried out using potassium t-butoxide in DMF.

10. The process according to claim 7, wherein in step c) at least 3 molar equivalents of said base are utilized.

11. The compound according to claim 6, wherein said compound is an intermediate reaction product.

* * * * *